United States Patent [19]

Garten et al.

[11] 4,140,487

[45] Feb. 20, 1979

[54] METHOD AND APPARATUS FOR ANALYSIS OF WATER

[75] Inventors: Victor A. Garten, Burwood; Robert McNeill, Hampton; Johannas M. Overbeek, Dandenong; Richard B. Head, Middle Brighton, all of Australia

[73] Assignee: Commonwealth Scientific and Industiral Research Organization, Campbell, Australia

[21] Appl. No.: 747,994

[22] Filed: Dec. 6, 1976

[30] Foreign Application Priority Data

Dec. 10, 1975 [AU] Australia ............................ PC4243

[51] Int. Cl.² ..................... G01N 31/00; G01N 33/18
[52] U.S. Cl. ....................................... 422/78; 422/58
[58] Field of Search ........................ 23/230 R, 253 R

[56] References Cited

U.S. PATENT DOCUMENTS

| 3,224,837 | 12/1965 | Moyat | 23/230 R |
| 3,296,435 | 1/1967 | Teal et al. | 250/304 |
| 3,647,387 | 3/1972 | Benson et al. | 23/232 R |

Primary Examiner—Robert M. Reese
Attorney, Agent, or Firm—Cushamn, Darby & Cushman

[57] ABSTRACT

A method for detecting the presence in water of substances which are rapidly oxidized by ozone with the emission of quanta of visible light, which method comprises contacting the water with ozone and detecting the light quanta emitted.

3 Claims, 5 Drawing Figures

METHOD AND APPARATUS FOR ANALYSIS OF WATER

This invention relates to a new method and apparatus for the detection, identification and quantitative analysis of certain organic and inorganic substances in water and waste waters.

The phrase "water and waste water" as used herein refers to any aqueous media but, in particular, such waters as sewage effluents, river and bay waters, industrial waters, drinking water, distilled water and water for injection. In other words, the invention is broadly concerned with the analysis of a very broad range of waters from those of the highest purity to those of the greatest pollutant content.

Many methods of analysis have been developed for determining the content of oxidisable materials in water; such methods include the determination of COD (Chemical Oxygen Demand), BOD (Biological Oxygen Demand), TOC (Total Organic Carbon), and TOD (Total Oxygen Demand). These methods differ greatly in nature and particularly in the times required for their performance. For example, determination of COD takes approximately 2 hours and determination of BOD approximately 5 days, while determination of TOC and TOD requires only about 2 minutes.

Further, even the more rapid of these techniques involve fairly complex equipment and are thus unsuitable for field work or continuous in situ monitoring on an automatic, unattended basis.

All of the above quoted methods involve substantially exhaustive oxidation of all or some oxidisable materials in the water and these methods therefore show roughly linear correlations to each other. (See for example "Carbon Measurements in Water Quality Monitoring" by Walter J. Maier and Hugh L. McConnell in "Journal of Water Pollution Control Federation", Volume 46, No. 4, April 1974, pages 623–633).

The present invention seeks to provide a totally new method of water analysis which is rapid and readily amenable to performance in the field, and on an unattended basis.

The invention also seeks to provide a method which provides unique information regarding the quality of water when taken alone or used in combination with the known methods of water analysis.

The present invention is based on our observation that when water containing certain organic or inorganic substances in solution or suspension is contacted with ozone, these substances are oxidised very rapidly by ozone with the emission of quanta of visible light.

The term "visible light" means that the light emitted has a wavelength in the visible region of the spectrum. It must be emphasised, however, that the amount of light emitted is very small and cannot be seen by the naked eye, except under the most ideal conditions with the dark-adapted eye.

The organic materials concerned are those which contain certain functional groups, the principal functional groups in question being SH groups (present in almost all proteins), phenolic OH groups and olefinic double bonds. Inorganic sulphides and ammonia also react rapidly with ozone to produce visible light quanta. Water which contains any organic substances having the groups indicated above and/or inorganic sulphides and/or ammonia will, on reaction with ozone, produce visible light quanta.

It is known that certain gaseous substances, notably ethylene, are oxidized by gaseous ozone with the emission of light and a known method for analysing gas mixtures containing very small quantities of ozone, e.g., in air, is based on this phenomenon. To the best of our knowledge, however, the reaction of ozone in aqueous solution with oxidizable substances with consequent light emission has not previously been observed or reported.

According to the present invention, therefore, there is provided a method for detecting the presence in water of substances which are rapidly oxidized by ozone with the emission of quanta of visible light, which method comprises contacting the water with ozone and detecting the light quanta emitted.

The method of the invention may be carried out either by bubbling ozone through a sample of the water to be tested or by first providing a solution of the ozone in distilled water and mixing this solution with the test sample.

Thus, in accordance with one embodiment of the invention, a measured quantity of the water to be tested is added to a solution of ozone in distilled water. The amount of the test solution added depends on the degree of contamination of the water, but generally would be from 0.1 to 10 cm$^3$ per 50 cm$^3$ of the ozone solution, i.e., the amount of the ozone solution is from 5 to 500 times the quantity of water under test.

The light output from the reaction has been found to be substantially independent of the amount of ozone, provided the latter is in excess. This requirement can be met under most circumstances, by passing ozonised air or oxygen through a 50 cm$^3$ sample of distilled water for more than 2 minutes.

We have found in model experiments with organic compounds containing SH groups, phenolic OH groups, or olefinic double bonds, and with inorganic sulphides and ammonia, that the light emitting reactions involving these substances take place very rapidly and are substantially complete within 15 to 20 seconds. Other light emitting reactions and dark reactions do occur, notably those involving the oxidation of carbon skeletons, e.g., aromatic rings,

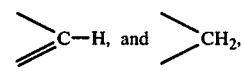

and of aliphatic OH and other groups. These reactions, however, take place slowly and continue for a relatively long period. We have found, however, that a count of photons emitted in the first 15 seconds of the reaction is linearly proportional to the amount of ozone consumed, and thus to the actual concentration of the SH and other active groups listed above.

Thus, in quantitative determinations, by the method of the invention, the light emitted from the mixed solutions as a result of the reaction is measured over a short standardised period, usually 15 seconds, after addition of the test sample. The amount of ozone in the distilled water solution should thus be in excess of the amount required to react with the water in a period of 15 seconds.

In the above-described embodiment, discrete samples of the water under test are used. However, in accordance with a further and preferred embodiment, the method of our invention may be performed on a continuous, on-stream basis by introducing a stream of ozone or ozonized air into a continuous stream of the water under test, provided the amount of ozone so introduced is in excess of that required for complete oxidation of the oxidisable substances in the water. The emitted photons are counted as before, the count being integrated over a standardized period, again usually 15 seconds.

To further illustrate the principles underlying the invention, we shall refer to one of the model compounds we have been in our experiments, namely ovalbumin, which is a gluco-protein containing SH groups. When a solution of ovalbumin is treated with a solution containing excess ozone, most of the light is emitted within 15 seconds. On the other hand, a solution of insulin (a protein which contains no SH groups) when similarly treated emits only very small quantities of light and then over a relatively long period. Moreover, with ovalbumin, the number of photons emitted during the reaction increases linearly with the concentration of the gluco-protein. It is possible to determine protein concentrations of less than 0.1 ppm.

The quantity of light emitted by the reaction of a certain quantity of water containing such active groups and for a particular optical geometry of the apparatus used, can easily be related to the total amount of ozone consumed (which can be determined chemically, e.g., by iodometry) and the total measured light can thus be expressed in terms of ozone consumed, i.e. as an "ozone demand". However, the number of photons emitted for a particular amount of ozone consumed can vary considerably from one mixture to another because of the possibility of ozone consuming but non-luminous reactions taking place, e.g. with compounds such as carbohydrates and hydrocarbons. With ovalbumin as the model substance, for example, it is found that 0.38 mg of ozone are consumed for each milligram of ovalbumin, the absolute number of photons emitted being about $4 \times 10^8$ (the optical geometry having been allowed for).

As well as providing an overall quantitative estimation of the reactive substances in solution, at least, under laboratory conditions, the method may be modified to differentiate between the groups giving rise to the light emission. For example, SH groups can be blocked, e.g. with N-ethyl malemide, to eliminate their contribution to light emission. The emission due to other substances or groups present can then be determined separately.

The invention also provides apparatus for carrying out the method of the invention, which apparatus broadly comprises a reaction vessel to contain a body of water, means for generating and supplying ozone to water in the vessel, means for introducing a test sample of water into the vessel, and means for detecting light emitted from the water in the vessel.

In one embodiment of the apparatus, the vessel initially contains distilled water which is first saturated with ozone. The test sample is then added to the distilled water.

In another embodiment, the vessel is adapted to allow a continuous flow of the water under test through the vessel and the ozone supply means is arranged to continuously inject ozone into the water stream while it passes through the vessel.

The detection means may be any suitable photo-electric device, but for quantitative measurements it must be capable of providing an electric signal which is related to the number of photons impinging on the device.

Reference will now be made to the accompanying drawings in which.

Figure 1:
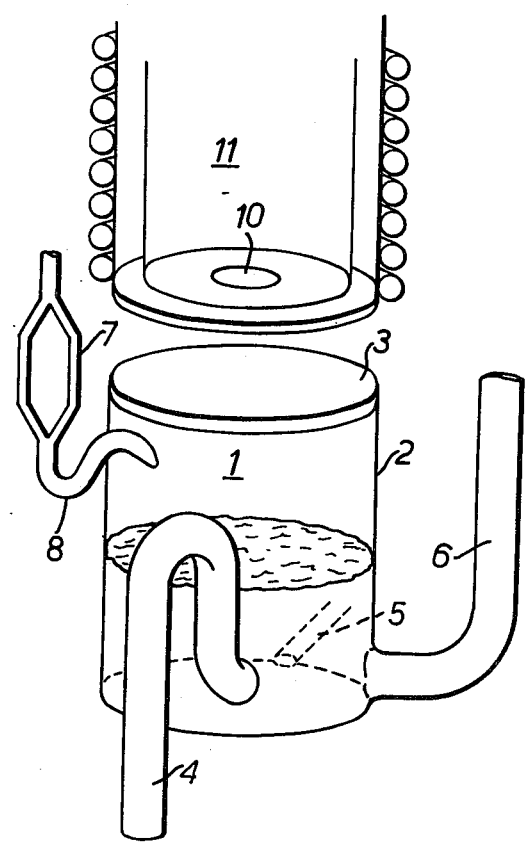
FIG. 1 is a diagrammatic representation of an apparatus in accordance with the invention.

In FIG. 1, the reactor 1 consists of a cylindrical vessel 2 made of glass or other ozone-resistant material and having a fixed lid 3 of optical-quality glass. The vessel 2 is provided with an overflow tube 4 and a gas entry tube 5 to admit ozonized air to the reactor near the base of the vessel 2. A water supply tube 6 is provided to enable fresh distilled water to be fed to the vessel when required.

A sample dispenser 7 (shown in part only) of a type known per se, e.g., Exelo Dispenser, Type DP/2VT is arranged to exhaust its contents through tube 8 into the vessel 2.

Facing the lid 3 is the window 10 of a water cooled photomultiplier tube 11 (shown in part only).

Operation of the apparatus is best described with reference to FIG. 2 which shows in block form the arrangement of a programmed water pollution monitor instrument for the fully automatic sequential testing of water quality in a body or stream of water.

The numbering of FIG. 1 is used to indicate the component of the reactor system, and the other components are described hereinafter.

In operation of the system, an aliquot of distilled water (typically 50 cm$^3$) is supplied from tank 20 to the reactor 1 through tube 6. Ozonized air is produced by passing air from pump 21 through an ozonizer 22 and the stream of ozonized air is bubbled through the water in the reactor 1 via tube 5 (about 2 minutes being sufficient to equilibrate 50 cm$^3$ of distilled water with ozone). During this period, the power supply 23 to the photomultiplier 11, and its associated pulse counting 24 and recording equipment 25 are switched on, (the photomultiplier being in complete darkness) to allow a steady background to be reached. The ozone supply to the reactor is then discontinued, the counter 24 is then reset and restarted and a measured sample of the test water is injected by the sample dispenser 7 into the reactor 1 through tube 8. Counting of the photo-induced pulses from the photomultiplier 11 is allowed to proceed for 15 seconds, after which the counter 24 is stopped and the reading printed out or otherwise recorded or signalled by the recorder 25.

After a suitable delay period e.g., about 10 minutes or any desired longer period, a further test cycle is initiated by recommencing the ozone flow to the reactor.

Water for cooling the photomultiplier 11 (to ensure stability) and for providing the test sample is drawn from the water source by a pump 27 from which it flows to the photomultiplier and a sample reservoir 28.

The entire operational sequence is controlled by a preset programmer 29.

At appropriate intervals, e.g. fortnightly when 12 hourly sampling is employed, fresh distilled water from the tank 20 is run through the reactor 1 to flush the system. Between flushings, the overflow pipe 4 ensures the presence of a sufficiently constant volume of water in the reactor 1.

It will be appreciated that a much simpler manually operated instrument can be constructed on the same principles as the fully automatic version described above. Such an instrument can, of course, dispense with the programmer and signal printout as well as the flushing tank, sample reservoir and automatic dispenser.

Figure 3:
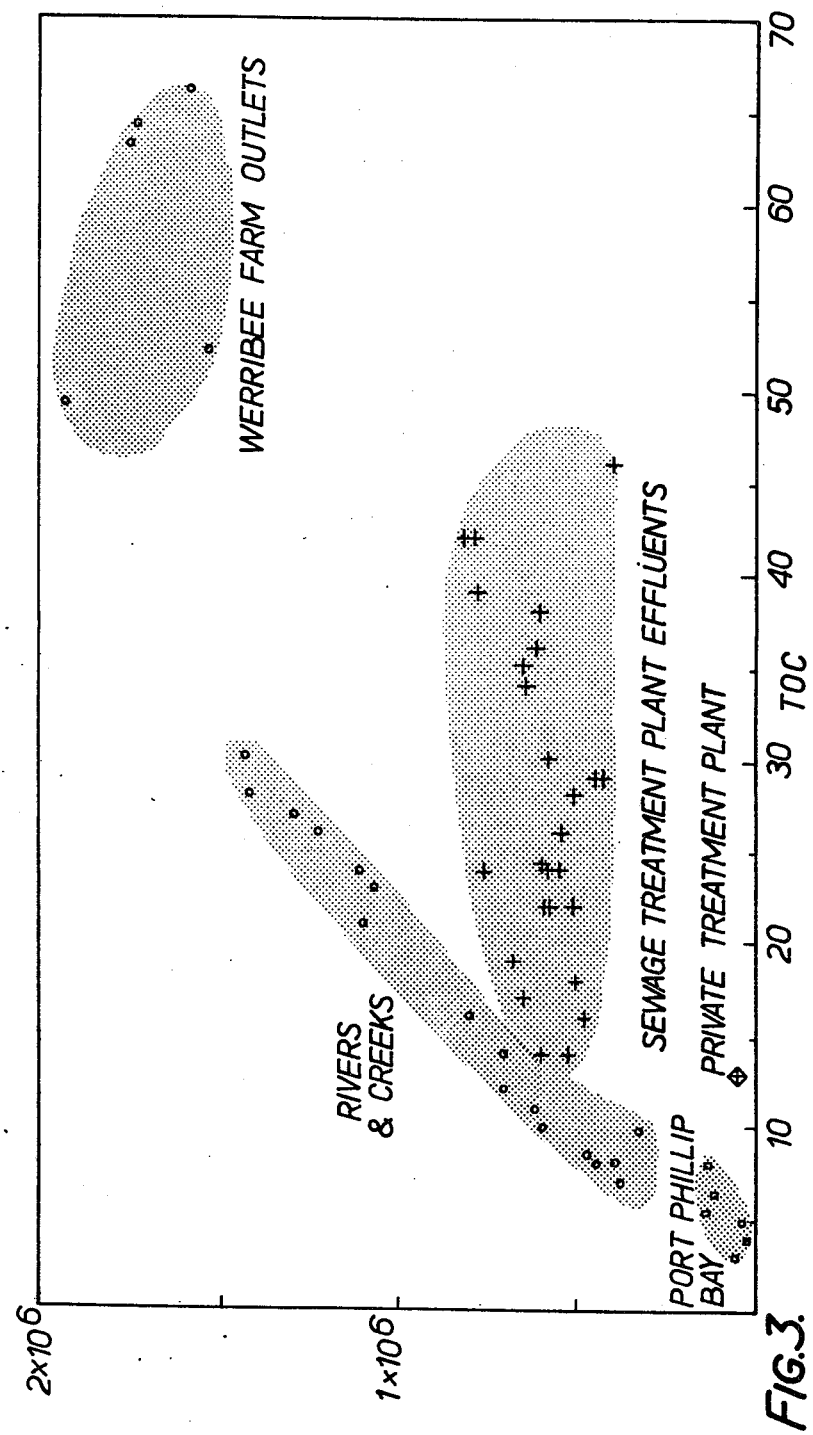
FIG. 3 is a graphical plot of results of water analysis obtained by the method of the invention and by the TOC method.

FIG. 3 shows some results obtained with various waters obtained in the Melbourne and metropolitan area using a more simple manually operated apparatus.

The graph of FIG. 3 plots the photon count for various samples (uncorrected for optical geometry) obtained under standard conditions from a 1 cm³ sample reacted with ozone-equilibrated distilled water, against the TOC figures of the same samples determined independently. Examination of FIG. 3 shows the following significant results:
1. No single simple relationship exists between the light emitted by samples and the TOC of the samples.
2. There is, however, a distinct general distribution of the plotted points depending on the type of water tested, for example:
   (a) Waters from rivers and creeks show a nearly linear relationship of photon count to TOC.
   (b) Samples of effluents from water purification plants with widely varying TOC figures show a medium and seemingly satisfactory level of obnoxious material as measured by the photon count, which is at a relative constant level.
   (c) Effluent from a sewage farm (at Werribee, Victoria) shows a distinctly different type of behaviour with photon count and TOC figures falling into a broad region of high photon count and high TOC.
   (d) A relatively small group of waters collected from various points on Port Phillip Bay, Victoria, exhibit simultaneously low levels of photon count and TOC.

Consideration of these points shows that in the event of contamination of a river by organic materials such as carbohydrates or hydrocarbons, a very large TOC reading, unaccompanied by any substantial rise in photon count would result, and this would act as an indicator of an abnormal change in composition.

It should be noted that none of the previously employed methods (COD, BOD, TOC or TOD) alone or in combination provide information regarding water quality which can now be obtained by the method of the invention. In particular, new and valuable information can be obtained by a combination of the present method with rapid and exhaustive methods of assessment such as TOC and the two methods together provide a two-dimensional expression of water quality.

Additionally, the present method alone gives a very useful measure of water quality and provides an accurate means of assessing the relative proportion of the easily oxidisable materials present in the water samples. Table I shows the photon counts for various water samples (not corrected for optical geometry).

TABLE I

| Location | Photon Count $\times 10^{-3}$ |
| --- | --- |
| Port Phillip Bay water samples (50m offshore) | 25 – 125 |
| Sewage Treatment Effluents | 200 – 800 |
| Various Rivers and Creeks (Melbourne Metropolitan Area) | 300 – 1400 |

TABLE I-continued

| Location | Photon Count $\times 10^{-3}$ |
| --- | --- |
| Effluent from Werribee Sewage Farm (various outlets) | 1150 – 1900 |

Since, as indicated above, the photons counted in the first 15 seconds after mixing are linearly proportional to the ozone consumed, and thus to the actual concentration of the active groups, the apparatus described above acts as a "proportional counter". The concentration of active groups is related to the ozone consumed and the photons emitted by the relations:

mg test material = $k_1 \times$ mg ozone consumed and
mg ozone consumed = $k_2 \times$ photons emitted where $k_1$ lies between 0.54 (for acetylene) and about 1000 for very inactive material and $k_2$ is approximately $(2.5 \pm 0.1) \times 10^{-10}$.

It will be appreciated from the above description that standardisation of the photomultiplier against slow variations of photocathode sensitivity with time, or for different cells with different photocathode sensitivity, is important. Various methods of standardisation are available but we prefer to use firstly, a chemical standard of a solution of ovalbumin with a concentration of 50ppm. In the particular system geometry we have studied and for an EMI 6256S (1 cm dia cathode) photomultiplier we obtained a count of 14,200. As a secondary standard, it is possible to use a light emitting diode (LED) which emits a green light. The diode is immersed in water at standard temperature and operated at a very small pre-selected current in a fixed optical geometry. This provides a luminous source of substantially constant output which can be used for calibration purposes.

Figure 4:
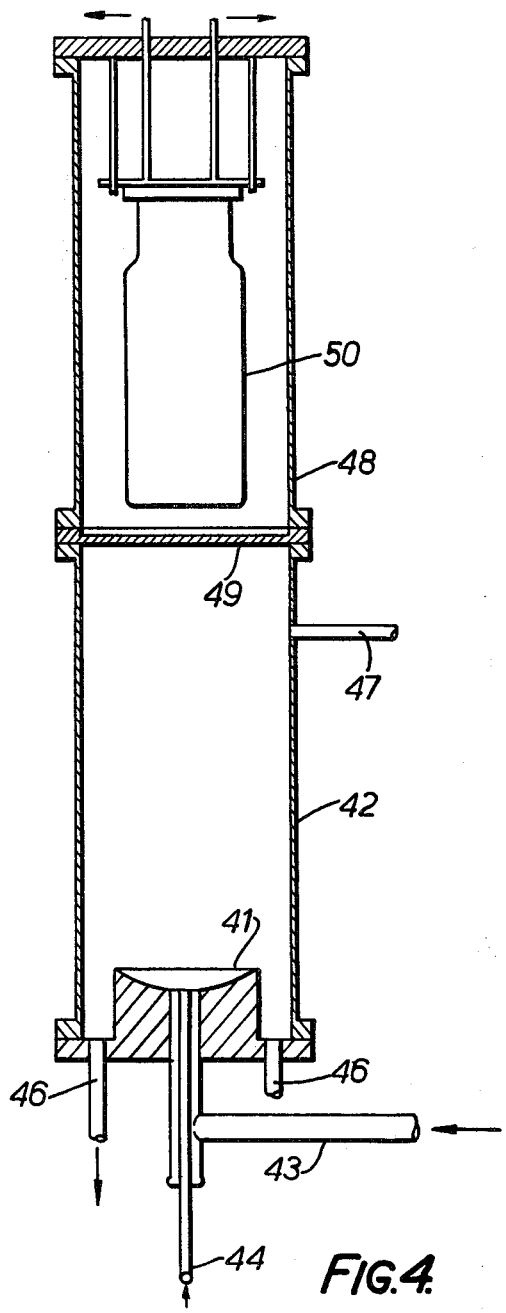
FIG. 4 is a diagrammatic representation of another form of apparatus in accordance with the invention.

FIG. 4 depicts a modified reactor vessel adapted for continuous flow-through operation. This vessel consists of a shallow cup-shaped flow cell 41 mounted at the base of a chamber 42. Concentric water and ozone inlet pipes 43, 44 enter the cup 41 at its base. Water entering the cup 41 through pipe 43 overflows the edges of the cup and runs down its sides to drain from the chamber 42 through pipes 46. A gas vent 47 is provided near the top of the chamber 42. A second chamber 48 is mounted mouth to mouth above the chamber 42, the two chambers being separated by an optical glass window 49. The second chamber 48 houses and provides protection and light shielding for a photomultiplier tube or similar photo-detecting device 50.

In operation of the apparatus, a stream of the water under test is pumped at a constant flow rate into the cup 41 through pipe 43 and continuously overflows and passes to waste through pipes 46. Ozone or ozonized air is introduced into the cell 41 through pipe 44 in a continuous stream and at a rate such that there is always present an amount of ozone in excess of that required for reaction with oxidation of substances in the water. The photomultiplier monitors the chemiluminescent emission from the water and its electrical output is over a period of about 15 seconds is integrated and amplified (by means not shown) to produce a suitable output for recording.

An apparatus of the kind just described finds particularly useful application in ozone demand monitoring systems used in water purification plants.

Ozone is commonly used in water treatment to reduce the amount of oxidizable materials and for sterilization of drinking water. It is difficult to monitor this process, and we are not aware of any continuously-operating, simple apparatus which will directly measure ozone demand. Fluctuations in the incoming raw water, if not detected, will result in inadequately sterilized water.

Figure 5:
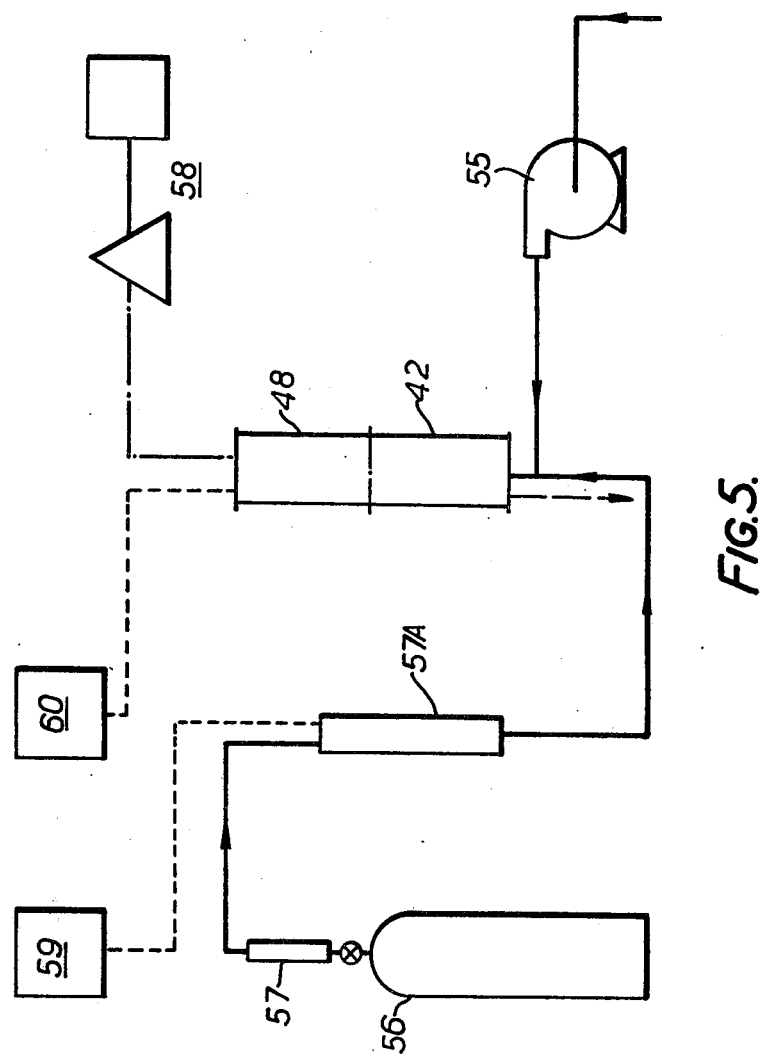
FIG. 5 is a block diagram of an ozone demand monitoring instrument embodying the apparatus of FIG. 4.

FIG. 5 shows diagrammatically an ozone demand monitoring system incorporating the apparatus of FIG. 4 (of which like parts are numbered as in FIG. 4). The system includes a metering pump 55, to supply the test water to the flow cell (in chamber 42), an oxygen supply 56, metering device 57 and ozonizer 57A, amplifier recorder and alarm means 58 associated with the photomultiplier (in chamber 48) and power supply means 59, 60 for the photomultiplier and ozonizer.

Figure 2:
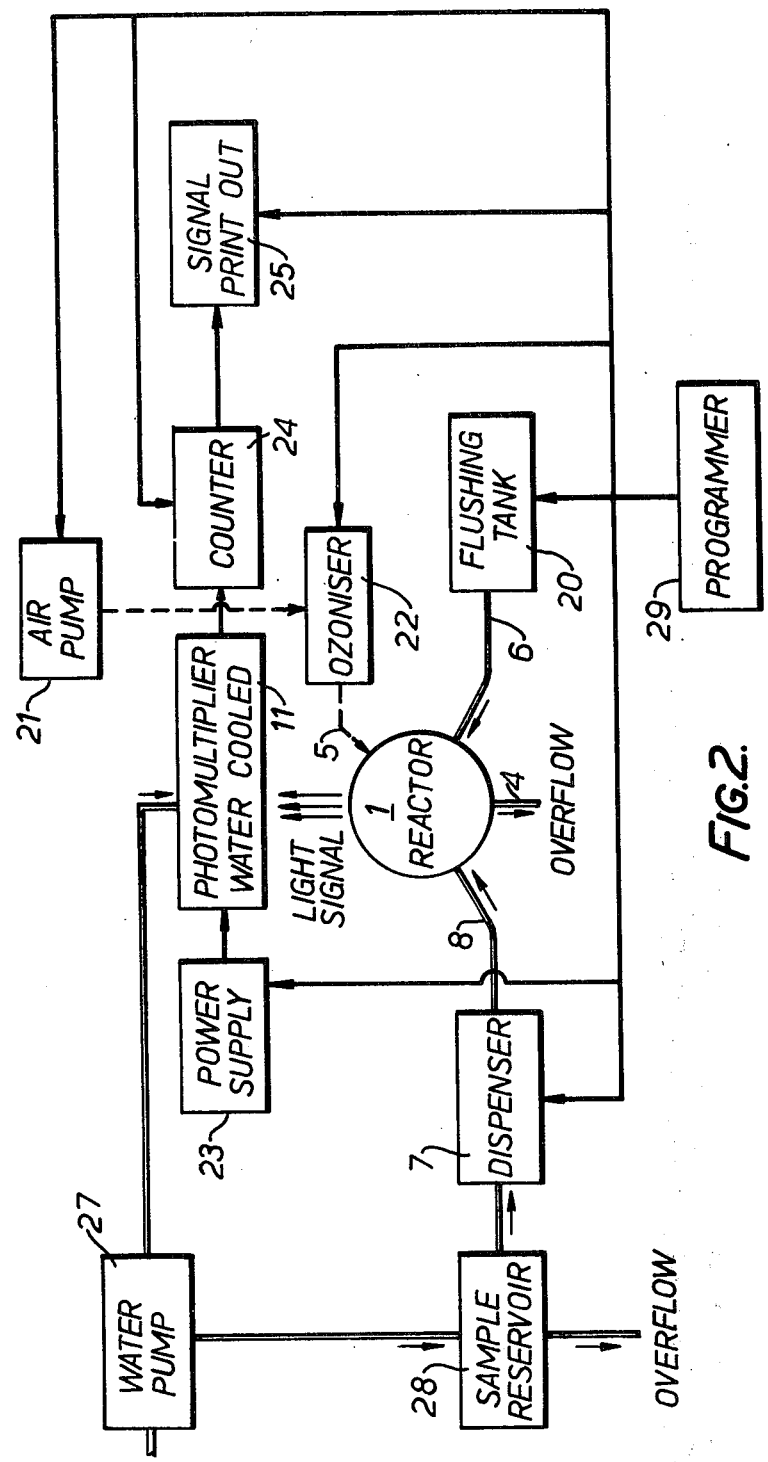
FIG. 2 is a block diagram of an integrated water monitoring system embodying the apparatus of FIG. 1.

The apparatus of FIG. 5 can be used to monitor a single water source, as with the apparatus of FIG. 2 or it can be used to give accurate continuous direct assessment of the performance of an ozonization water treatment plant. In the latter case, the operation involves simultaneously sampling the treated water and either a sample of the raw water or a sample of the treated water which has been further saturated with ozone. The two samples are analysed continuously in the apparatus of FIG. 5, and a comparison of the outputs provides a measure of the effectiveness of the ozone treatment. This output can be readily used to control the ozonization and to increase or decrease the amount of ozone treatment.

We claim:

1. Apparatus for detecting the presence in water of substances which are rapidly oxidized by ozone with the emission of quanta of visible light, comprising a reactor vessel for containing a body of water, said reactor vessel being made of ozone resistant material, having a fixed lid of optical-quality glass, and being provided with gas and water inlet tubes and an overflow tube for water outlet; water supply means to supply distilled water to the vessel through said water inlet tube; air supply means comprising a pump and ozonizer to generate and supply ozonized air to the vessel through said gas inlet tube; sample dispensing means to dispense a measured volume of the water to be tested into the vessel; and light detection and measuring means for detecting light emitted from the water in the vessel comprising a water cooled photomultiplier facing said window and associated power supply and pulse counting means.

2. Apparatus as claimed in claim 1 and further including programming means to enable the apparatus to perform its operations automatically in sequence, recording means to automatically record the results, and flushing means to periodically flush the vessel with clean distilled water.

3. Apparatus as claimed in claim 1, wherein the reaction vessel consists of an open cup.

* * * * *